United States Patent
Kalla et al.

(10) Patent No.: US 7,625,881 B2
(45) Date of Patent: Dec. 1, 2009

(54) PRODRUGS OF $A_{2B}$ ADENOSINE RECEPTOR ANTAGONISTS

(75) Inventors: Rao Kalla, Sunnyvale, CA (US); Dmitry Koltun, Foster City, CA (US); Jeff Zablocki, Mountain View, CA (US); Elfatih Elzein, Fremont, CA (US)

(73) Assignee: Gilead Palo Alto, Inc., Foster City, CA (US)

( * ) Notice: Subject to any disclaimer, the term of this patent is extended or adjusted under 35 U.S.C. 154(b) by 459 days.

(21) Appl. No.: 11/453,414

(22) Filed: Jun. 14, 2006

(65) Prior Publication Data

US 2006/0293283 A1 Dec. 28, 2006

Related U.S. Application Data

(60) Provisional application No. 60/691,408, filed on Jun. 16, 2005.

(51) Int. Cl.
*C07D 473/06* (2006.01)
*C07D 473/08* (2006.01)
*A61K 31/522* (2006.01)
*A61P 1/12* (2006.01)
*A61P 11/06* (2006.01)
*A61P 9/10* (2006.01)

(52) U.S. Cl. ............... 514/81; 514/263.2; 544/244; 544/270

(58) Field of Classification Search ............ 514/81, 514/263.2; 544/244, 270
See application file for complete search history.

(56) References Cited

U.S. PATENT DOCUMENTS

| | | | |
|---|---|---|---|
| 3,845,770 A | 11/1974 | Theeuwes et al. | |
| 4,326,525 A | 4/1982 | Swanson et al. | |
| 4,902,514 A | 2/1990 | Barclay et al. | |
| 4,992,445 A | 2/1991 | Lawter et al. | |
| 5,001,139 A | 3/1991 | Lawter et al. | |
| 5,023,252 A | 6/1991 | Hseih | |
| 5,616,345 A | 4/1997 | Geoghegan et al. | |
| 6,117,878 A * | 9/2000 | Linden | 514/263.34 |
| 6,825,349 B2 | 11/2004 | Kalla et al. | |
| 6,894,021 B2 * | 5/2005 | Belardinelli et al. | 514/263.2 |
| 6,977,300 B2 | 12/2005 | Kalla et al. | |
| 7,125,993 B2 | 10/2006 | Elzein et al. | |
| 2007/0219221 A1 * | 9/2007 | Zeng et al. | 514/263.2 |
| 2008/0293705 A1 * | 11/2008 | Wilson et al. | 514/227.8 |

OTHER PUBLICATIONS

"Respiratory experts call for global approach to treat chronic disease" (European Respiratory Society, Feb. 13, 2007) <http://www.med-wire-news.md/48/64443/Respiratory/Respiratory_experts_call_for_global_approach_to_treat_chronic_disease.html> downloaded from the internet Mar. 17, 2009.*

"Role of Pneumocystis in COPD Progression" (2005) <http://www.trdrp.org/research/PageGrant.asp?grant_id=4019> dowloaded from the internet Mar. 17, 2009.*

* cited by examiner

*Primary Examiner*—Mark L Berch
(74) *Attorney, Agent, or Firm*—J. Elin Hartrum; Daniel W. Collins; Brian Lewis

(57) ABSTRACT

Disclosed are prodrugs of $A_{2B}$ adenosine receptor antagonists, having the following structure

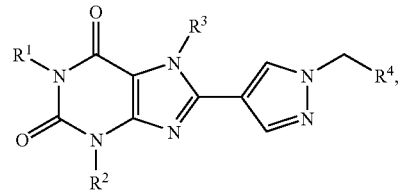

and their use in treating mammals for various disease states.

17 Claims, No Drawings

PRODRUGS OF $A_{2B}$ ADENOSINE RECEPTOR ANTAGONISTS

Priority is claimed to U.S. Provisional Patent Application Ser. No. 60/691,408, filed Jun. 16, 2005, the complete disclosure of which is hereby incorporated by reference.

FIELD OF THE INVENTION

The present invention relates to prodrugs of $A_{2B}$ adenosine receptor antagonists, and to their use in treating mammals for various disease states, such as gastrointestinal disorders, immunological disorders, hypersensitivity disorders, neurological disorders, and cardiovascular diseases due to both cellular hyperproliferation and apoptosis, and the like. The invention also relates to methods for the preparation of such compounds, and to pharmaceutical compositions containing them.

BACKGROUND

Adenosine is a naturally occurring nucleoside, which exerts its biological effects by interacting with a family of adenosine receptors known as $A_1$, $A_{2A}$, $A_{2B}$, and $A_3$, all of which modulate important physiological processes. For example, $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, Drug Dev Res 45:198; Feoktistov et al., Trends Pharmacol Sci 19:148-153), and $A_3$ adenosine receptors modulate cell proliferation processes.

Adenosine $A_{2B}$ receptors are ubiquitous, and regulate multiple biological activities. For example, adenosine binds to $A_{2B}$ receptors on endothelial cells, thereby stimulating angiogenesis. Adenosine also regulates the growth of smooth muscle cell populations in blood vessels. Adenosine stimulates $A_{2B}$ receptors on mast cells, thus modulating Type I hypersensitivity reactions. Adenosine also stimulates gastrosecretory activity by ligation with $A_{2B}$ in the intestine.

While many of these biological effects of adenosine are necessary to maintain normal tissue homeostasis, under certain physiological changes it is desirable to modulate its effects. For example, the binding of $A_{2B}$ receptors stimulates angiogenesis by promoting the growth of endothelial cells. Such activity is necessary in healing wounds, but the hyperproliferation of endothelial cells promotes diabetic retinopathy. Also, an undesirable increase in blood vessels occurs in neoplasia. Accordingly, inhibition of the binding of adenosine to $A_{2B}$ receptors in the endothelium will alleviate or prevent hypervasculation, thus preventing retinopathy and inhibiting tumor formation.

$A_{2B}$ receptors are found in the colon in the basolateral domains of intestinal epithelial cells, and when acted upon by the appropriate ligand act to increase chloride secretion, thus causing diarrhea, which is a common and potentially fatal complication of infectious diseases such as cholera and typhus. $A_{2B}$ antagonists can therefore be used to block intestinal chloride secretion, and are thus useful in the treatment of inflammatory gastrointestinal tract disorders, including diarrhea.

Insensitivity to insulin exacerbates diabetes and obesity. Insulin sensitivity is decreased by the interaction of adenosine with $A_{2B}$ receptors. Thus, blocking the adenosine $A_{2B}$ receptors of individuals with diabetes or obesity would benefit patients with these disorders.

Another adverse biological effect of adenosine acting at the $A_{2B}$ receptor is the over-stimulation of cerebral IL-6, a cytokine associated with dementias and Alzheimer's disease. Inhibiting the binding of adenosine to $A_{2B}$ receptors would therefore mitigate those neurological disorders that are produced by IL-6.

Type I hypersensitivity disorders, such as chronic obstructive pulmonary disease (COPD), asthma, hay fever, and atopic eczema, are stimulated by mast cells binding to $A_{2B}$-receptors. Accordingly, blocking such adenosine receptors provides a therapeutic benefit against such disorders.

There are several compounds presently used in the treatment of asthma. For example, theophylline is an effective anti-asthmatic agent, even though it is a poor adenosine receptor antagonist. However, high plasma levels are needed for it to be effective. Additionally, theophylline has substantial side effects, most of which are due to its CNS action, which provide no beneficial effects in the treatment of asthma, and to the fact that it non-specifically blocks all adenosine receptor subtypes.

Additionally adenosine treatment, such as inhaled adenosine (or adenosine monophosphate), provokes bronchoconstriction in asthmatics, but not in the normal population. This process is known to involve mast cell activation, in that it releases mast cell mediators, including histamine, PGD2-β-hexosaminidase and tryptase. This response is blocked by specific histamine $H_1$ blockers and chromolyn sodium. Accordingly, there is an intrinsic difference in the way adenosine interacts with mast cells from asthmatics, and thus $A_{2B}$ antagonists are particularly useful in modulating mast cell function or in the activation of human lung cells.

U.S. Pat. No. 6,825,349 discloses novel $A_{2B}$ adenosine receptor antagonists that are potent and selective for the $A_{2B}$ adenosine receptor. A category of preferred compounds disclosed in the above patent application has been identified in which the 7-position of the xanthine moiety is unsubstituted. Such compounds are known to be relatively insoluble in aqueous media and difficult to formulate using conventional pharmaceutical excipients, and thus potentially difficult to formulate in a manner that provides reproducible plasma levels of the compound undergoing evaluation in mammals, in particular humans. We have discovered compounds that are more soluble in aqueous media and/or conventional pharmaceutical excipients, and are surprisingly active as prodrugs of the compounds of '349.

SUMMARY OF THE INVENTION

U.S. Pat. No. 6,825,349 discloses novel $A_{2B}$ adenosine receptor antagonists. One embodiment of the invention of '349 is represented by the following formula:

Formula A

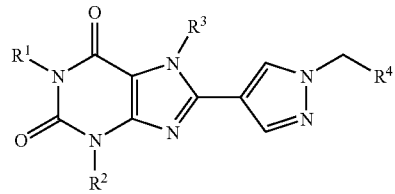

in which:
$R^1$ and $R^2$ are independently lower alkyl;
$R^3$ is hydrogen or optionally substituted alkyl; and
$R^4$ is optionally substituted phenyl;
and the pharmaceutically acceptable salts thereof.

One preferred embodiment of compounds within the scope of Formula A includes those compounds in which the 7-position of the xanthine moiety is unsubstituted; that is, where $R^3$ is hydrogen. Particularly preferred are those compounds in which $R^1$ and $R^2$ are different, and are lower alkyl, and $R^4$ is 3-trifluoromethylphenyl. However, it has been found that the preferred compounds are relatively insoluble in aqueous media and difficult to formulate using conventional pharmaceutical excipients, and thus potentially difficult to formulate in a manner that provides reproducible plasma levels of a compound undergoing evaluation in mammals, in particular humans. It has surprisingly been discovered that a small subset of compounds of Formula A behave as prodrugs of the preferred compounds. These compounds are chosen from compounds of Formula A in which $R^3$ is substituted methyl; in particular, those compounds in which the substitution on the methyl provides an ester or a phosphate derivative. Such compounds are more soluble in aqueous media and/or conventional pharmaceutical excipients than the compounds of Formula A, and provide higher plasma levels of the active moiety (those compounds of Formula A in which $R^3$ is hydrogen) than administration of the active moiety itself.

Accordingly, in a first aspect, the present invention relates to prodrugs of Formula I having the formula:

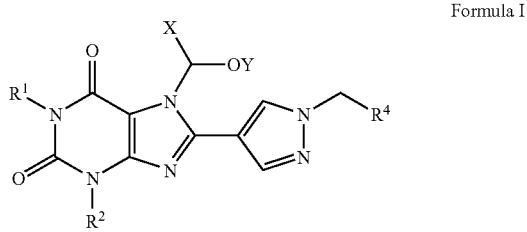

Formula I wherein:
$R^1$ and $R^2$ are independently lower alkyl;
$R^4$ is optionally substituted phenyl;
X is hydrogen or methyl; and
Y is —C(O)R, in which R is independently optionally substituted lower alkyl, optionally substituted aryl, or optionally substituted heteroaryl; or
Y is —P(O)(OR$^5$)$_2$, in which $R^5$ is hydrogen or lower alkyl optionally substituted by phenyl or heteroaryl;
and the pharmaceutically acceptable salts thereof.

One preferred group of compounds of Formula I are those in which $R^1$ and $R^2$ are ethyl or n-propyl, especially those compounds in which $R^1$ is n-propyl and $R^2$ is ethyl. Preferably $R^4$ is 3-(trifluoromethyl)phenyl and X is hydrogen.

One preferred subgroup includes those compounds of Formula I in which Y is —C(O)R, particularly those compounds in which R is methyl, ethyl, n-propyl, isopropyl, n-butyl, isobutyl, t-butyl, or n-pentyl, more particularly where R is methyl, n-propyl, or t-butyl. Another preferred subgroup includes those compounds of Formula I in which Y is —P(O)OR$^5$)$_2$, especially where $R^5$ is hydrogen.

In a second aspect, the present invention relates to a method of using the compounds of Formula I for treating a disease state in a mammal that is alleviable by treatment with an $A_{2B}$ adenosine receptor antagonist, in particular atherosclerosis, angiogenesis, diabetic retinopathy, cancer, chronic obstructive pulmonary disease, or asthma, or inflammatory gastrointestinal tract disorders such as diarrhea, or neurological disorder such as senile dementia, Alzheimer's disease, or Parkinson's disease.

A third aspect of this invention relates to methods for preparing the compounds of Formula I.

A fourth aspect of this invention relates to pharmaceutical formulations, comprising a therapeutically effective amount of a compound of Formula I and at least one pharmaceutically acceptable excipient.

At present, the preferred compounds are:
[3-ethyl-2,6-dioxo-1-propyl-8-(1-{[3-(trifluoromethyl)phenyl]methyl}pyrazol-4-yl)-1,3,7-trihydropurin-7-yl]methyl acetate;
[3-ethyl-2,6-dioxo-1-propyl-8-(1-{[3-(trifluoromethyl)phenyl]methyl}pyrazol-4-yl)-1,3,7-trihydropurin-7-yl]methyl 2,2-dimethylpropanoate;
[3-ethyl-2,6-dioxo-1-propyl-8-(1-{[3-(trifluoromethyl)phenyl]methyl}pyrazol-4-yl)-1,3,7-trihydropurin-7-yl]methyl butanoate; and
[3-ethyl-2,6-dioxo-1-propyl-8-(1-{[3-(trifluoromethyl)phenyl]methyl}-pyrazol-4-yl)(1,3,7-trihydropurin-7-yl)]methyl dihydrogen phosphate.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, phosphate, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or 2) an alkyl group as defined above that is interrupted by 1-10 atoms independently chosen from oxygen, sulfur and NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both 1, 2, 3, 4 or 5 substituents as defined above and is also interrupted by 1-10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1-10 carbon atoms, more preferably 1, 2, 3, 4, 5 or 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

The term "lower alkylene" refers to a diradical of a branched or unbranched saturated hydrocarbon chain, preferably having from 1, 2, 3, 4, 5, or 6 carbon atoms.

The term "lower alkylene" refers to a diradical of a branched or unbranched saturated hydrocarbon chain, preferably having from 1, 2, 3, 4, 5, or 6 carbon atoms.

The term "substituted alkylene" refers to:
(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or
(2) an alkylene group as defined above that is interrupted by 1-20 atoms independently chosen from oxygen, sulfur and $NR_a$—, where $R_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylene (—$CH(NH_2)CH_2$—), methylaminoethylene (—CH(NHMe)$CH_2$—), 2-carboxypropylene isomers(—$CH_2CH(CO_2H)CH_2$—), ethoxyethyl (—$CH_2CH_2O$—$CH_2CH_2$—), ethylmethylaminoethyl (—$CH_2CH_2N(CH_3)CH_2CH_2$—), 1-ethoxy-2-(2-ethoxy-ethoxy)ethane (—$CH_2CH_2O$—$CH_2CH_2$—$OCH_2CH_2$—$OCH_2CH_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH=$CH_2$), 1-propylene or allyl (—$CH_2CH$=$CH_2$), isopropylene (—$C(CH_3)$=$CH_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or prop-1-yn-3-yl, —$CH_2C$≡CH), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, $CF_3$, amino, substituted amino, cyano, or —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained by the definition for the aryl or arylene substituent, such aryl or arylene groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl, Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, $CF_3$, amino, substituted amino, cyano, or —S(O)$_n$R, in which R is alkyl, aryl, or heteroaryl and n is 0, 1 or 2.

The term "cycloalkyl" refers to carbocyclic groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroarylene" refers to a diradical of a heteroaryl group as defined above. This term is exemplified by groups such as 2,5-imidazolene, 3,5-[1,2,4]oxadiazolene, 2,4-oxazolene, 1,4-pyrazolene, and the like. For example, 1,4-pyrazolene is:

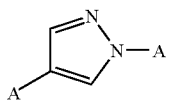

where A represents the point of attachment.

Unless otherwise constrained by the definition for the heteroaryl or heteroarylene substituent, such heteroaryl or heterarylene groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, -SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, prodrugs, hydrates and polymorphs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

As used herein, the term "prodrug" denotes a compound that is metabolized in-vivo to a compound that is active as an $A_{2B}$ adenosine receptor antagonist.

Nomenclature

The naming and numbering of the compounds of the invention is illustrated with a representative compound of Formula I in which $R^1$ is n-propyl, $R^2$ is ethyl, $R^4$ is 3-trifluorophenyl, X is hydrogen, and Y is —C(O)CH$_2$CH$_2$CH$_3$;

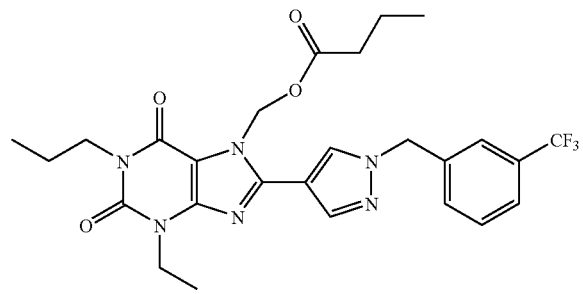

which is named:
[3-ethyl-2,6-dioxo-1-propyl-8-(1-{[3-(trifluoromethyl)phenyl]methyl}pyrazol-4-yl)-1,3,7-trihydropurin-7-yl]methyl butanoate.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents. The term "q.s." means adding a quantity sufficient to achieve a stated function, e.g., to bring a solution to the desired volume (i.e., 100%).

Synthesis of the Compounds of Formula I

A method for preparing compounds of Formula I in which Y is optionally substituted lower alkyl, optionally substituted aryl, or optionally substituted heteroaryl is shown in Reaction Scheme I.

REACTION SCHEME I

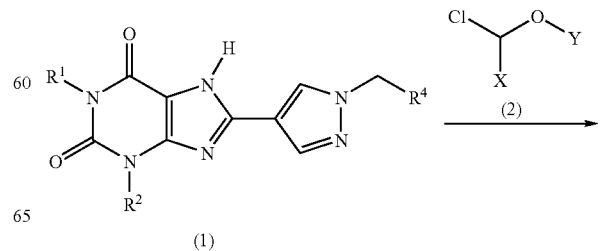

-continued

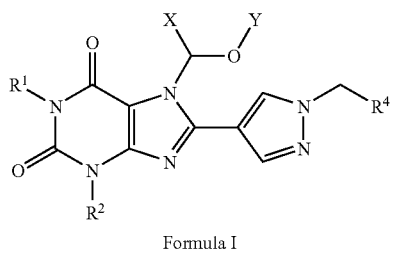

Formula I where $R^1$, $R^2$, $R^4$, X and Y are as defined above.

In general, the compound of formula (1) is reacted in a polar solvent, for example N,N-dimethylformamide, with a compound of formula YOCHXCl. The reaction is carried out at a temperature of about 30 to 80° C., preferably about 60° C., in the presence of a base, preferably an inorganic base, for example potassium carbonate, for about 8-24 hours. When the reaction is substantially complete, the product of Formula I is isolated by conventional means, for example preparative chromatography.

The starting compound of formula (1) can be prepared by those techniques disclosed in U.S. Pat. No. 6,825,349, or those disclosed in U.S. patent application Ser. No. 10/719, 102, publication number 20040176399, the entire contents of which are hereby incorporated by reference.

When Y is —C(O)R, in which R is a heterocycle, the compound of formula (2) (RC(O)OCHXCl) is either commercially available or can be prepared as shown below, using pyridine as an example.

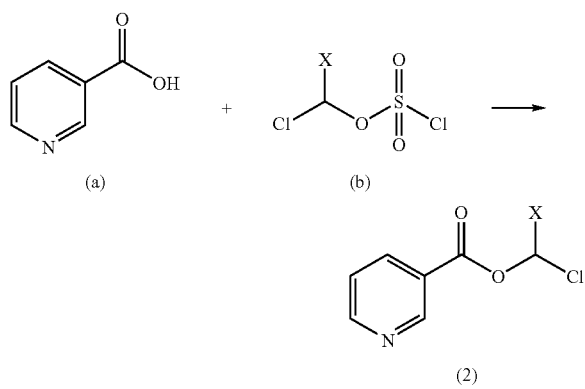

In general, the carboxylic acid of formula (a) is reacted in an inert solvent, for example dichloromethane, with a chloromethyl derivative of formula (b) in the presence of a quarternary salt, for example tetrabutylammonium sulfate. The reaction is carried out at a temperature of about 0° C., in the presence of a base, preferably an inorganic base, for example sodium bicarbonate, followed by reaction at room temperature for about 2-10 hours. When the reaction is substantially complete, the product, chloromethyl pyridine-3-carboxylate, is isolated by conventional means.

Carbamate derivatives can be prepared as shown in Reaction Scheme II.

REACTION SCHEME II

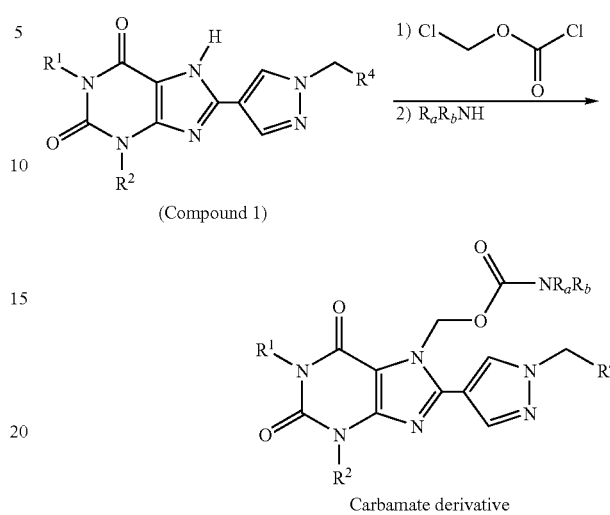

Carbamate derivative where $R^1$, $R^2$ and $R^4$, are as defined above, and $R_aR_bNH$ represents an amine.

In general, the amine of formula $R_aR_bNH$ is reacted in a polar solvent, for example N,N-dimethylformamide, with chloromethyl chloroformate at a temperature of about 0° C., in the presence of a base, preferably an inorganic base, for example potassium carbonate, for about 1 hour. Then a solution of the compound of formula (1) in a polar solvent at 0° C. is added, and the mixture reacted for 24 hours, allowing the temperature to rise to room temperature. When the reaction is substantially complete, the product of Formula I is isolated by conventional means, for example preparative chromatography.

To prepare an ether derivative of a compound of formula (1), the compound of formula (1) is reacted conventionally with an appropriate chloromethyl ether.

A method for preparing compounds of Formula I in which Y is —P(O)(OH)$_2$ is shown in Reaction Scheme III.

REACTION SCHEME III

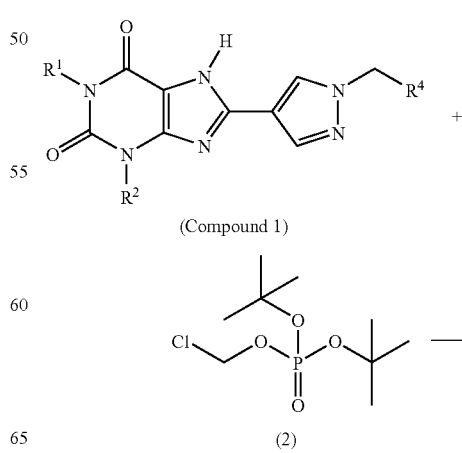

-continued (3)

Compound of Formula I

Step 1

In general, the compound of formula (2) is reacted with a compound of formula (1) in a polar solvent, for example N,N-dimethylformamide, at a temperature of about 30-90° C., in the presence of a base, preferably an inorganic base, for example potassium carbonate, for about 4-24 hours. When the reaction is substantially complete, the product of formula (3) is isolated by conventional means and purified, for example preparative chromatography.

Step 2

The product of formula (3) is deprotected conventionally with a strong acid, for example trifluoroacetic acid, or alternatively a weak acid such as formic acid, in an inert solvent, for example dichloromethane. The reaction is conducted at about room temperature for about 4-24 hours. When the reaction is substantially complete, the product of Formula I in which Y is —P(O)(OH)$_2$ is isolated by conventional means and purified, for example preparative chromatography.

Starting Material of Formula (2)

The compound of formula (2), di-tert-butyl chloromethyl phosphate, is prepared from bis(tert-butoxy)phosphino-1-ol as shown below.

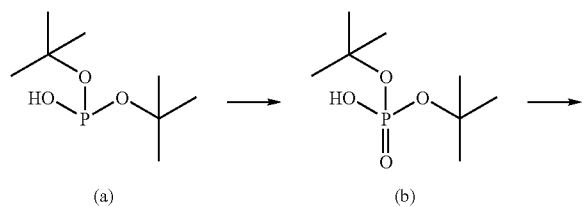

(a)  (b)

-continued (2)

Step 1

In general, the compound of formula (a), bis(tert-butoxy) phosphino-1-ol, is reacted with an oxidizing, for example potassium permanganate, in the presence of a mild base, for example potassium bicarbonate, in an aqueous solvent. The reaction is initially conducted at a temperature of about 0° C., and then at about room temperature for about 1 hour. When the reaction is substantially complete, the product of formula (b), di-tert-butyl hydrogen phosphate, is isolated by conventional means, for example by acidification and filtration of the phosphate thus formed.

Step 2

Initially a tetramethylammonium salt of (b) is prepared by reaction of di-tert-butyl hydrogen phosphate with tetramethylammonium hydroxide in an inert solvent, for example acetone, at a temperature of about 0° C. The tetramethylammonium salt of di-tert-butyl hydrogen phosphate is isolated by conventional means, for example by removal of the solvent.

The tetramethylammonium salt of di-tert-butyl hydrogen phosphate is then reacted with a dihalomethane derivative, for example dibromomethane or chloroiodomethane, in an inert solvent, for example 1,2-dimethoxyethane. The reaction is conducted at a temperature of about 60-90° C. When the reaction is substantially complete, the product of formula (2) is isolated by conventional means.

Utility, Testing and Administration

General Utility

The compounds of Formula I are effective in-vivo for the treatment of conditions that respond to administration of A$_{2B}$ adenosine receptor antagonists. Such conditions include, but are not limited to, at least one of diarrhea, atherosclerosis, restenosis, diabetic retinopathy, cancer, senile dementia, Alzheimer's disease, Parkinson's disease, traumatic brain injury, and Type I hypersensitivity reactions, including chronic obstructive pulmonary disease (COPD), asthma, atopic eczema, and hay fever.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modern Pharmaceutics", Marcel Dekker, Inc. 3$^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50-200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid reformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula I

Preparation of a Compound of Formula I where $R^1$ is n-Propyl, $R^2$ is Ethyl, $R^4$ is 3-Trifluoromethylphenyl, X is Hydrogen, and Y is n-Butanoyl

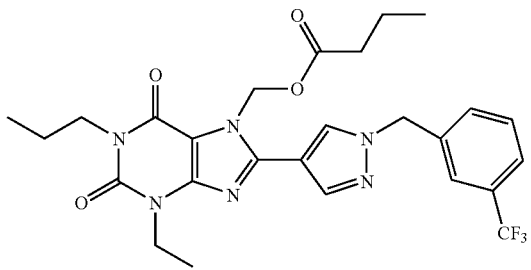

To a solution of 3-ethyl-1-propyl-8-(1-{[3-(trifluoromethyl)phenyl]methyl}-pyrazol-4-yl)-1,3,7-trihydropurine-2,6-dione (250 mg, 0.56 mmol) in N,N-dimethylformamide (10 ml) was added potassium carbonate (230 mg, 1.68 mmol), followed by chloromethylbutyrate (230 mg, 1.68 mmol), and the mixture was stirred at 60° C. for 16 hours. The solid was filtered off, and solvent removed from the filtrate under reduced pressure. The residue was chromatographed on silica gel, eluting with 30% ethyl acetate/hexane, yielding [3-ethyl-2,6-dioxo-1-propyl-8-(1-{[3-(trifluoromethyl)phenyl]methyl}pyrazol-4-yl)-1,3,7-trihydropurin-7-yl]methyl butanoate (150 mg). $^1$H NMR (CDCl$_3$): δ 7.98 (s, 1H), 7.97 (s, 1H), 7.65-7.45 (m, 4H), 6.35 (s, 2H), 5.44 (s, 2H), 4.19 (q, J=8 Hz, 2H), 3.98 (q, J=2 Hz, 2H), 2.33 (t, J=8 Hz, 2H), 1.75-1.60 (m, 4H), 1.36 (t, J=8 Hz, 3H), 0.96 (t, J=8 Hz, 3H), 0.92 (t, J=8 Hz, 3H).

B. Preparation of Other Compounds of Formula I

Similarly, following the procedure of 1A above, but replacing chloromethylbutyrate by chloromethyl-2,2-dimethylpropanoate, [3-ethyl-2,6-dioxo-1-propyl-8-(1-{[3-(trifluoromethyl)phenyl]methyl}pyrazol-4-yl)-1,3,7-trihydropurin-7-yl]methyl-2,2-dimethylpropanoate was prepared. $^1$H NMR (CDCl$_3$): δ 7.98 (s, 1H), 7.97 (s, 1H), 7.65-7.45 (m, 4H), 6.33 (s, 2H), 5.43 (s, 2H), 4.19 (q, J=8 Hz, 2H), 3.98 (q, J=2 Hz, 2H), 1.75-1.64 (m, 2H), 1.37 (t, J=8 Hz, 3H), 1.16 (s, 9H), 0.96 (t, J=8 Hz, 3 H).

Similarly, following the procedure of 1A above, but replacing chloromethylbutyrate by chloromethyl acetate, [3-ethyl-2,6-dioxo-1-propyl-8-(1-{[3-(trifluoromethyl)phenyl]methyl}pyrazol-4-yl)-1,3,7-trihydropurin-7-yl]methyl acetate was prepared. $^1$H NMR (CDCl$_3$): δ 7.98 (s, 1H), 7.97 (s, 1H), 7.65-7.45 (m, 4H), 6.35 (s, 2H), 5.44 (s, 2H), 4.19 (q, J=8 Hz, 2H), 3.98 (q, J=2 Hz, 2H), 2.33 (t, J=8 Hz, 2H), 1.75-1.60 (m, 4H), 1.36 (t, J=8 Hz, 3H), 0.96 (t, J=8 Hz, 3H), 0.92 (t, J=8 Hz, 3H).

Similarly, following the procedure of 1A above, but replacing chloromethylbutyrate by chloro(2S)-1-[benzyloxycarbonyl]pyrrolidine-2-carboxylate, [3-ethyl-2,6-dioxo-1-propyl-8-(1-{[3-(trifluoromethyl)phenyl]methyl}pyrazol-4-yl)-1,3,7-trihydropurin-7-yl]methyl (2S)-1-[benzyloxycarbonyl]pyrrolidine-2-carboxylate was prepared. The NMR of this compound was satisfactory.

C. Preparation of Other Compounds of Formula I

Similarly, following the procedure of 1A above, but replacing chloromethylbutyrate by other compounds of the formula YOCHXCl, in which X and Y are as defined above, the following compounds of Formula I are prepared:

[3-ethyl-2,6-dioxo-1-propyl-8-(1-{[3-(trifluoromethyl)phenyl]methyl}pyrazol-4-yl)-1,3,7-trihydropurin-7-yl]methyl 2-methylpropanoate;

[3-ethyl-2,6-dioxo-1-propyl-8-(1-{[3-(trifluoromethyl)phenyl]methyl}pyrazol-4-yl)-1,3,7-trihydropurin-7-yl]methyl benzoate;

[3-ethyl-2,6-dioxo-1-propyl-8-(1-{[3-(trifluoromethyl)phenyl]methyl}pyrazol-4-yl)-1,3,7-trihydropurin-7-yl]methyl 3-(trifluoromethyl)benzoate;

[3-ethyl-2,6-dioxo-1-propyl-8-(1-{[3-(trifluoromethyl)phenyl]methyl}pyrazol-4-yl)-1,3,7-trihydropurin-7-yl]methyl 2-phenylacetate;

[3-ethyl-2,6-dioxo-1-propyl-8-(1-{[3-(trifluoromethyl)phenyl]methyl}pyrazol-4-yl)-1,3,7-trihydropurin-7-yl]ethyl butanoate;

[3-ethyl-2,6-dioxo-1-propyl-8-(1-{[3-(trifluoromethyl)phenyl]methyl}pyrazol-4-yl)-1,3,7-trihydropurin-7-yl]methyl propanoate;

[3-ethyl-2,6-dioxo-1-propyl-8-(1-{[3-(trifluoromethyl)phenyl]methyl}pyrazol-4-yl)-1,3,7-trihydropurin-7-yl]methyl pentanoate;

[3-ethyl-2,6-dioxo-1-propyl-8-(1-{[3-(trifluoromethyl)phenyl]methyl}pyrazol-4-yl)-1,3,7-trihydropurin-7-yl]methyl hexanoate;

[3-ethyl-2,6-dioxo-1-propyl-8-(1-{[3-(trifluoromethyl)phenyl]methyl}pyrazol-4-yl)-1,3,7-trihydropurin-7-yl]methyl octanoate;

[3-ethyl-2,6-dioxo-1-propyl-8-(1-{[3-(trifluoromethyl)phenyl]methyl}pyrazol-4-yl)-1,3,7-trihydropurin-7-yl]methyl 3-methylbutanoate;

[3-ethyl-2,6-dioxo-1-propyl-8-(1-{[3-(trifluoromethyl)phenyl]methyl}pyrazol-4-yl)-1,3,7-trihydropurin-7-yl]methyl cyclopentanecarboxylate;

[3-ethyl-2,6-dioxo-1-propyl-8-(1-{[3-(trifluoromethyl)phenyl]methyl}pyrazol-4-yl)-1,3,7-trihydropurin-7-yl]methyl cyclohexanecarboxylate;

2-({[3-ethyl-2,6-dioxo-1-propyl-8-(1-{[3-(trifluoromethyl)phenyl]methyl}pyrazol-4-yl)-1,3,7-trihydropurin-7-yl]methyl}oxycarbonyl)acetic acid;

3-({[3-ethyl-2,6-dioxo-1-propyl-8-(1-{[3-(trifluoromethyl) phenyl]methyl}pyrazol-4-yl)-1,3,7-trihydropurin-7-yl] methyl}oxycarbonyl)propanoic acid;

[3-ethyl-2,6-dioxo-1-propyl-8-(1-{[3-(trifluoromethyl)phenyl]methyl}pyrazol-4-yl)-1,3,7-trihydropurin-7-yl]methyl 3-methoxypropanoate;

[3-ethyl-2,6-dioxo-1-propyl-8-(1-{[3-(trifluoromethyl)phenyl]methyl}pyrazol-4-yl)-1,3,7-trihydropurin-7-yl]methyl 3-hydroxybutanoate;

[3-ethyl-2,6-dioxo-1-propyl-8-(1-{[3-(trifluoromethyl)phenyl]methyl}pyrazol-4-yl)-1,3,7-trihydropurin-7-yl]methyl 3-(oxyphosphinyloxyphosphinyl)butanoate;

[3-ethyl-2,6-dioxo-1-propyl-8-(1-{[3-(trifluoromethyl)phenyl]methyl}pyrazol-4-yl)-1,3,7-trihydropurin-7-yl]methyl 3-[(oxyphosphinyloxyphosphinyl)methoxy]butanoate;

[3-ethyl-2,6-dioxo-1-propyl-8-(1-{[3-(trifluoromethyl)phenyl]methyl}pyrazol-4-yl)-1,3,7-trihydropurin-7-yl]methyl benzoate;

[3-ethyl-2,6-dioxo-1-propyl-8-(1-{[3-(trifluoromethyl)phenyl]methyl}pyrazol-4-yl)-1,3,7-trihydropurin-7-yl]methyl 4-piperazinylbenzoate;

[3-ethyl-2,6-dioxo-1-propyl-8-(1-{[3-(trifluoromethyl)phenyl]methyl}pyrazol-4-yl)-1,3,7-trihydropurin-7-yl]methyl 4-morpholin-4-ylbenzoate; and

[3-ethyl-2,6-dioxo-1-propyl-8-(1-{[3-(trifluoromethyl)phenyl]methyl}pyrazol-4-yl)-1,3,7-trihydropurin-7-yl]methyl pyridine-3-carboxylate.

EXAMPLE 2

Preparation of a Carbamate Derivative of a Compound of Formula (1)

Preparation of [3-ethyl-2,6-dioxo-1-propyl-8-(1-{[3-(trifluoromethyl)phenyl]methyl}-pyrazol-4-yl)-1,3,7-trihydropurin-7-yl]methyl 4-methylpiperazinecarboxylate

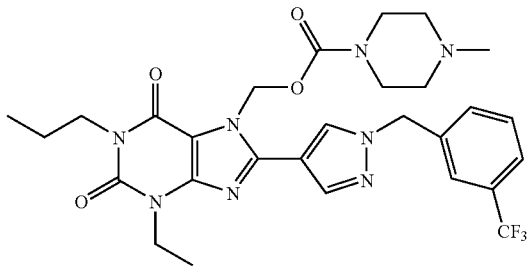

Chloromethyl chloroformate (0.319 mmol) and 1-methylpiperazine (0.319 mmol) were mixed in N,N-dimethylformamide (2 ml) at 0° C. in the presence of potassium carbonate (1.325 mmol). After 1 hour, a precooled solution of 3-ethyl-1-propyl-8-(1-{[3-(trifluoromethyl)phenyl]methyl}-pyrazol-4-yl)-1,3,7-trihydropurine-2,6-dione (0.265 mmol) in N,N-dimethylformamide (1 ml) was added, and the mixture was stirred for 24 hours, allowing the temperature to rise to room temperature. Solvent was removed under reduced pressure, and the residue applied to a preparative thin layer chromatography plate, eluting with 5% methanol/methylene chloride, providing 150 mg of [3-ethyl-2,6-dioxo-1-propyl-8-(1-{[3-(trifluoromethyl)phenyl]methyl}pyrazol-4-yl)-1,3,7-trihydropurin-7-yl]methyl 4-methylpiperazinecarboxylate.

Similarly, the following compounds were prepared:

N-[2-(dimethylamino)ethyl]{[3-ethyl-2,6-dioxo-1-propyl-8-(1-{[3-(trifluoromethyl)phenyl]methyl}pyrazol-4-yl)(1,3,7-trihydropurin-7-yl)]methoxy}-carboxamide;

N-[2-(dimethylamino)ethyl] {[3-ethyl-2,6-dioxo-1-propyl-8-(1-{[3-(trifluoromethyl)phenyl]methyl}pyrazol-4-yl)(1,3,7-trihydropurin-7-yl)]methoxy}-N-methylcarboxamide; and N-[((2S)-1-ethyl(2-piperidyl))methyl]{[3-ethyl-2,6-dioxo-1-propyl-8-(1-{[3-(trifluoromethyl)phenyl]methyl}pyrazol-4-yl)(1,3,7-trihydropurin-7-yl)]methoxy}carboxamide.

EXAMPLE 3

Preparation of a Phosphate Derivative of a Compound of Formula (1)

Preparation of [3-ethyl-2,6-dioxo-1-propyl-8-(1-{[3-(trifluoromethyl)phenyl]methyl}-pyrazol-4-yl)(1,3,7-trihydropurin-7-yl)]methyl Dihydrogen Phosphate

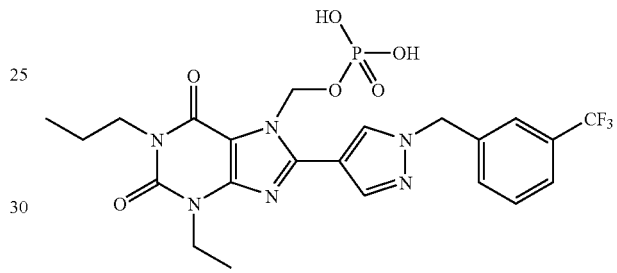

Step 1—Preparation of di-tert-butyl Chloromethyl Phosphate (Formula (2))

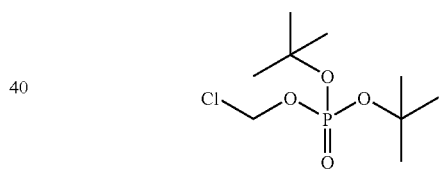

(2)

a) Preparation of di-tert-butyl hydrogen phosphate

To a stirred solution of bis(tert-butoxy)phosphino-1-ol (0.78 g, 4 mmol) and potassium bicarbonate (0.6 g, 2.4 mmol) in water (4 ml) at 0° C. was added (in portions) potassium permanganate (0.44 g, 2.8 mmol). The mixture was allowed to warm to room temperature, and stirred for 1 hour. Decolorizing charcoal (60 mg) was then added, and the mixture stirred at 60° C. for 15 minutes, and then filtered. The solid thus obtained was washed with water (30 ml), and the combined filtrates were treated with a further 100 mg of decolorizing charcoal at 60° C. for 20 minutes. The mixture was filtered, and the filtrate cooled to 0° C. and carefully acidified with concentrated hydrochloric acid (2 ml) with stirring. The precipitate was filtered off, washed with cold water, to provide di-tert-butyl hydrogen phosphate as a white solid.

Preparation of the Tetramethylammonium Salt of di-tert-butyl Hydrogen Phosphate

A solution of the di-tert-butyl hydrogen phosphate obtained in step a) was dissolved in acetone (10 ml) and cooled to 0° C. To this solution was added a 10% aqueous solution of tetramethylammonium hydroxide (2.4 ml, 2.6 mmol), and the homogeneous solution was evaporated under reduced pressure to provide a solid, which was crystallized from refluxing 1,2-dimethoxyethane to provide tetramethylammonium di-tert-butyl hydrogen phosphate as a white solid.

The tetramethylammonium di-tert-butyl hydrogen phosphate obtained in step b was dissolved in refluxing 1,2-dimethoxymethane (15 ml), and chloroiodomethane (3.2 g, 18.1 mmol) added, and the mixture was refluxed for 90 minutes. The solvent was removed under reduced pressure, and the residue, di-tert-butyl chloromethyl phosphate, was used as such without further purification.

Step 2

A solution of 3-ethyl-1-propyl-8-(1-{[3-(trifluoromethyl)phenyl]methyl}-pyrazol-4-yl)-1,3,7-trihydropurine-2,6-dione (0.47 g, 1 mmol) was dissolved in 20 ml of N,N-dimethylformamide, and potassium carbonate (0.42 g, 4 mmol) was added, followed by di-tert-butyl chloromethyl phosphate (0.34 g, 1.32 mmol), and the mixture was stirred at 60° C. overnight. The reaction mixture was cooled, and the precipitate filtered off, washing with ethyl acetate. The filtrate was concentrated under reduced pressure, and the residue was purified by preparative thin layer chromatography, eluting with 4% methanol/methylene chloride, to provide tert-butyl [3-ethyl-2,6-dioxo-1-propyl-8-(1-{[3-(trifluoromethyl)phenyl]methyl}pyrazol-4-yl)(1,3,7-trihydropurin-7-yl)]methyl methylethyl phosphate (0.26 g) as a colorless oil.

Step 3

A solution of tert-butyl [3-ethyl-2,6-dioxo-1-propyl-8-(1-{[3-(trifluoromethyl)phenyl]methyl}pyrazol-4-yl)(1,3,7-trihydropurin-7-yl)]methyl methylethyl phosphate (80 mg, 0.12 mmol) was dissolved in methylene chloride (6 ml) and trifluoroacetic acid (0.72 mmol) was added. The mixture was stirred at room temperature overnight. The solvent was removed under reduced pressure, and the solid white residue was triturated with ether and collected by filtration, providing [3-ethyl-2,6-dioxo-1-propyl-8-(1-{[3-(trifluoromethyl)phenyl]methyl}-pyrazol-4-yl)(1,3,7-trihydropurin-7-yl)]methyl dihydrogen phosphate (41 mg).

NMR $^1$H-NMR (DMSO-d6) δ 8.70 (s, 1H), 8.15 (s, 1H), 7.74 (s, 1H), 7.69-7.71 (m, 1H), 7.60-7.63 (m, 2H), 6.12 (d, 2H, J=5.4 Hz), 5.54 (s, 2H), 4.06 (q, 2H, J=13.8 Hz), 3.84 (t, 2H, J=7.4 Hz), 1.52-1.62 (m, 2H), 1.25 (t, 3H, J=7.0 Hz), 0.87 (t, 3H, J=7.4 Hz); MS m/z 579.02 (M$^+$+Na)

EXAMPLE 4

Preparation of a Compound of Formula (1)

Preparation of a Compound of Formula I in which R$^1$ is n-Pro yl, R$^2$ is Ethyl, R$^4$ is 3-Trifluoromethylphenyl, X is Hydrogen, and Y is n-Butanoyl A. Preparation of chloromethyl pyridine-3-carboxylate

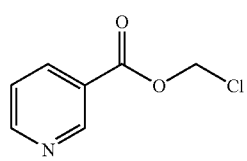

A mixture of nicotinic acid (200 mg, 1.6 mmol), sodium bicarbonate (540 mg, 6.4 mmol), and tetrabutylammonium sulfate (54 mg, 0.16 mmol) was dissolved in a mixture of 4 ml of dichloromethane and 4 ml of water, and cooled to 0° C. To this stirred mixture was added chloromethylchlorosulfone (165 µl, 1.6 mmol) in 1 ml of dichloromethane, and the mixture was allowed to warm to room temperature, stirring overnight. The organic layer was separated, washed with brine, dried over sodium sulfate, and concentrated under reduced pressure to a yellow oil, which was dissolved in dichloromethane and filtered through a silica plug. Removal of the solvent under reduced pressure provided chloromethyl pyridine-3-carboxylate (70 mg).

B. Preparation of [3-ethyl-2,6-dioxo-1-propyl-8-(1-{[3-(trifluoromethyl)phenyl]-methyl}pyrazol-4-yl)-1,3,7-trihydropurin-7-yl]methyl pyridine-3-carboxylate

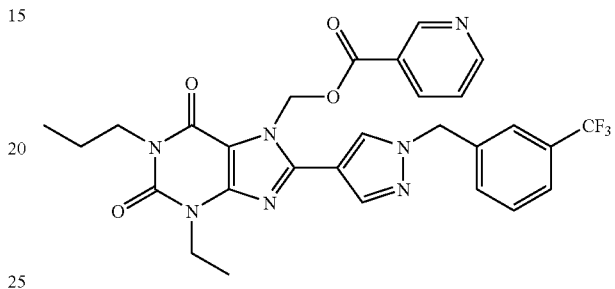

A solution of 3-ethyl-1-propyl-8-(1-{[3-(trifluoromethyl)phenyl]methyl}-pyrazol-4-yl)-1,3,7-trihydropurine-2,6-dione (200 mg, 0.43 mmol) was dissolved in 2 ml of N,N-dimethylformamide, and potassium carbonate (120 mg, 0.86 mmol) was added, followed by chloromethyl pyridine-3-carboxylate (220 mg, 1.3 mmol). The mixture was stirred at 60° C. overnight, the solid material filtered off, and the filtrate evaporated under reduced pressure. The residue was purified by thin layer chromatography, eluting with 5% methanol/dichloromethane, to provide [3-ethyl-2,6-dioxo-1-propyl-8-(1-{[3-(trifluoromethyl)phenyl]methyl}pyrazol-4-yl)-1,3,7-trihydropurin-7-yl]methyl pyridine-3-carboxylate (66 mg).

NMR of the product was satisfactory.

EXAMPLE 5

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

EXAMPLE 6

A tablet formula is prepared using the ingredients below:

| Ingredient | Quantity (mg/tablet) |
|---|---|
| Active Ingredient | 25.0 |
| Cellulose, microcrystalline | 200.0 |

-continued

| Ingredient | Quantity (mg/tablet) |
| --- | --- |
| Colloidal silicon dioxide | 10.0 |
| Stearic acid | 5.0 |

The components are blended and compressed to form tablets.

EXAMPLE 7

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 8

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 9

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 10

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 11

A subcutaneous formulation may be prepared as follows:

| Ingredient | Quantity |
| --- | --- |
| Active Ingredient | 5.0 mg |
| Corn Oil | 1.0 mL |

EXAMPLE 12

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5–6) |
| water (distilled, sterile) | q.s. to 1.0 ml |
| Nitrogen Gas, NF | q.s. |

EXAMPLE 13

A topical preparation is prepared having the following composition:

| Ingredients | grams |
| --- | --- |
| Active ingredient | 0.2–10 |
| Span 60 | 2.0 |

-continued

| Ingredients | grams |
|---|---|
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 14

$A_{2B}$ Adenosine Receptor Assays

Methods

Radioligand Binding for $A_{2B}$ Adenosine Receptor

Human $A_{2B}$ adenosine receptor cDNA is stably transfected into HEK-293 cells (referred to as HEK-$A_{2B}$ cells). Monolayer of HEK-$A_{2B}$ cells are washed with PBS once and harvested in a buffer containing 10 mM HEPES (pH 7.4), 10 mM EDTA and protease inhibitors. These cells are homogenized in polytron for 1 minute at setting 4 and centrifuged at 29000 g for 15 minutes at 4° C. The cell pellets are washed once with a buffer containing 10 mM HEPES (pH7.4), 1 mM EDTA and protease inhibitors, and are resuspended in the same buffer supplemented with 10% sucrose. Frozen aliquots are kept at −80° C. Competition assays are started by mixing 10 nM $^3$H-ZM214385 (Tocris Cookson) with various concentrations of test compounds and 50 μg membrane proteins in TE buffer (50 mM Tris and 1 mM EDTA) supplemented with 1 Unit/mL adenosine deaminase. The assays are incubated for 90 minutes, stopped by filtration using Packard Harvester and washed four times with ice-cold TM buffer (10 mM Tris, 1 mM MgCl2, pH 7.4). Non specific binding is determined in the presence of 10 μM ZM214385. The affinities of compounds (i.e. Ki values) are calculated using GraphPad software.

Radioligand Binding for Other Adenosine Receptors

Human $A_1$, $A_{2A}$, $A_3$ adenosine receptor cDNAs are stably transfected into either CHO or HEK-293 cells (referred to as CHO-A1, HEK-A2A, CHO-A3). Membranes are prepared from these cells using the same protocol as described above. Competition assays are started by mixing 0.5 nM $^3$H-CPX (for CHO-A1), 2 nM $^3$H-ZM214385 (HEK-A2A) or 0.1 nM $^{125}$I-AB-MECA (CHO-A3) with various concentrations of test compounds and the perspective membranes in TE buffer (50 mM Tris and 1 mM EDTA of CHO-A1 and HEK-A2A) or TEM buffer (50 mM Tris, 1 mM EDTA and 10 mM MgCl2 for CHO-A3) supplemented with 1 Unit/mL adenosine deaminase. The assays are incubated for 90 minutes, stopped by filtration using Packard Harvester and washed four times with ice-cold TM buffer (10 mM Tris, 1 mM MgCl2, pH 7.4). Non specific binding is determined in the presence of 1 μM CPX (CHO-A1), 1 μM ZM214385 (HEK-A2A) and 1 μM IB-MECA (CHO-A3). The affinities of compounds (i.e. Ki values) are calculated using GraphPad software.

cAMP Measurements

Monolayer of transfected cells is collected in PBS containing 5 mM EDTA. Cells are washed once with DMEM and resuspended in DMEM containing 1 Unit/mL adenosine deaminase at a density of 100,000-500,000 cells/ml. 100 μl of the cell suspension is mixed with 25 μl containing various agonists and/or antagonists and the reaction is kept at 37° C. for 15 minutes. At the end of 15 minutes, 125 μl 0.2N HCl is added to stop the reaction. Cells are centrifuged for 10 minutes at 1000 rpm. 100 μl of the supernatant is removed and acetylated. The concentrations of cAMP in the supernatants is measured using the direct cAMP assay from Assay Design.

$A_{2A}$ and $A_{2B}$ adenosine receptors are coupled to Gs proteins and thus agonists for $A_{2A}$ adenosine receptor (such as CGS21680) or for $A_{2B}$ adenosine receptor (such as NECA) increase the cAMP accumulations whereas the antagonists to these receptors prevent the increase in cAMP accumulations-induced by the agonists. $A_1$ and $A_3$ adenosine receptors are coupled to Gi proteins and thus agonists for $A_1$ adenosine receptor (such as CPA) or for $A_3$ adenosine receptor (such as IB-MECA) inhibit the increase in cAMP accumulations-induced by forskolin. Antagonists to $A_1$ and $A_3$ receptors prevent the inhibition in cAMP accumulations.

EXAMPLE 15

Comparison of Bioavailability of $A_{2B}$ Adenosine Receptor Prodrugs vs $A_{2B}$ Adenosine Receptor Antagonist The following studies were conducted in order to compare the pharmacokinetics of the parent $A_{2B}$ adenosine receptor antagonist and its corresponding prodrug. The parent compound chosen was the compound of formula A in which $R^1$ is n-propyl, $R^2$ is ethyl, $R^3$ is hydrogen, and $R^4$ is 3-trifluoromethylphenyl; that is:

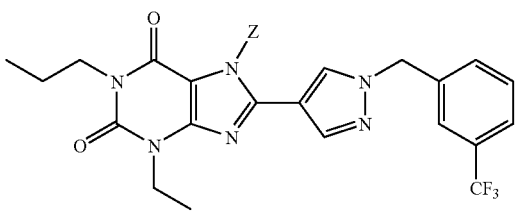

where Z is hydrogen (compound 1).

The prodrugs chosen for comparison were as follows:

where Z is —CH$_2$—O—C(O)CH$_2$CH$_2$CH$_3$ (compound 2);

where Z is —CH$_2$—O—C(O)CH$_3$ (compound 3);

where Z is —CH$_2$—O—C(O)C(CH$_3$)$_3$ (compound 4);

where Z is —CH$_2$—O—C(O)N(CH$_3$)CH$_2$CH$_2$N(CH$_3$)$_2$ (compound 5);

where Z is —CH$_2$—O—P(O)(OH)$_2$ (compound 6)

(compound 7)

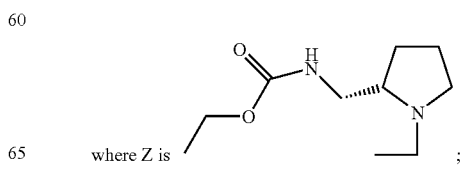

where Z is

-continued

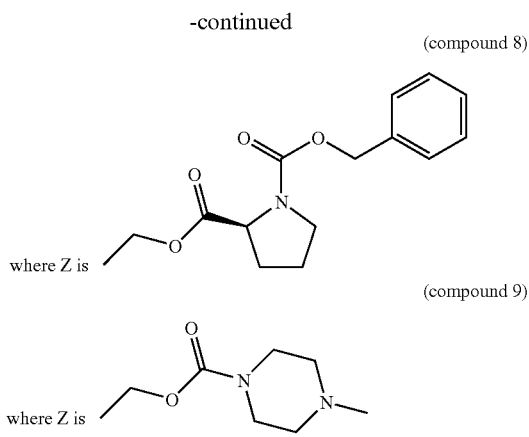

where Z is (compound 8)

where Z is (compound 9)

where Z is where Z is —CH$_2$—O—C(O)NHCH$_2$CH$_2$N(CH$_3$)$_2$ (compound 10);
where Z is —CH$_2$—OCH$_3$ (compound 11) and;
where Z is methyl (compound 12).

Reaction Monitoring (MRM) mode, monitoring the transitions at m/z 447.1>159.1 for compound 1 and 452.1>159.1 for I.S. The quantification limit of the assay was 0.38 ng/mL for the analysis of the oral dose samples and 10 ng/mL during the analysis of the intravenous dose samples using 0.1 mL of plasma.

Pharmacokinetic Analysis

Non-compartmental pharmacokinetic parameters were determined using a commercial program WinNonLin Professional, Version 4.1 (Pharsight, Mountain View, Calif.). Plasma concentration at below level of detection was assumed to be zero for the calculation of means and pharmacokinetic parameters.

For oral administration, the maximum concentration ($C_{max}$) and time to reach $C_{max}$ ($T_{max}$), $AUC_{(0-t)}$, $AUC_{(0-\infty)}$ and bioavailability (% F) were determined. Oral bioavailability was determined from the ratio of dose-adjusted $AUC_{(0-\infty)}$ of the respective oral dose and the mean $AUC_{(0-\infty)}$ values of the 0.1 and 0.5 mg/kg intravenous doses.

The results are presented below in tabular form. The table provides results obtained by using a suspension of the test compound in a suspension in DMSO/ethanol/PEG300/0.1% N-methyl-D-glucamine in rats.

|  | Prodrug | | Compound 1 | |
| --- | --- | --- | --- | --- |
| Compound | Mean Dose Adjusted AUC | Mean Cmax (ng/ml) | Mean Dose Adjusted AUC | Mean Cmax (ng/ml) |
| Compound 1 | Not applicable | Not applicable | 700 | 1,900 |
| Compound 2 | Not detectable | <5 ng/ml | 13,790 | 3,220 |
| Compound 3 | Not detectable | <5 ng/ml | 9,993 | 1,767 |
| Compound 4 | Not detectable | <5 ng/ml | 5,476 | 1,008 |
| Compound 5 | Not detectable | <5 ng/ml | 2,021 | 466 |
| Compound 6 | Not detectable | <5 ng/ml | 11,800 | 28,700 |
| Compound 7 | 51.0 | 30.0 | 1,817 | 408 |
| Compound 8 | Not detectable | <5 ng/ml | 1,089 | 241 |
| Compound 9 | 4.57 | 6.39 | 1,062 | 160 |
| Compound 10 | Not detectable | <5 ng/ml | 384 | 36.9 |
| Compound 11 | 533 | 158 | Not detectable | <5 ng/ml |
| Compound 12 | 926 | 279 | Not detectable | <5 ng/ml |

The studies were carried out in Sprague Dawley rats. The test compounds were administered orally by gavage to groups of three rats using a single oral dose of the test compound at 2 and 30 mg/kg. All oral doses were prepared either as a suspension in DMSO/ethanol/PEG300/0.1% N-methyl-D-glucamine or as a suspension in 0.5% methylcellulose in water. Blood samples were obtained serially from each rat at 0, 5, 15, 30 min, and then 1, 1.5, 2, 4, 6, 8, and 24 hrs post-dose.

Determination of Concentrations of Compound 1 and the Corresponding Prodrug in Plasma Concentrations of compound 1 and/or the corresponding prodrug in rat plasma were determined by a HPLC tandem mass spectrometric (LC/MS/MS) method. Briefly, 0.1 mL of plasma sample was treated with 0.5 mL of acetonitrile:methanol (9:1, v/v) mixture containing 25 ng of compound 1 having deuterated ethyl at the 3-position in place of ethyl. (Internal Standard, I.S.) to precipitate the protein. The mixture was filtered through a 96-well filter and filtrate was collected and evaporated to dryness on a 96-well plate evaporator. The residue was then reconstituted with 400 μL 20% methanol and subjected to LC/MS/MS analysis. Quantification of compound 1 was achieved by mass spectrometry using Multiple When administration was carried out in a suspension in 0.5% methylcellulose in water in rats at 30 mg/kg, compound 6 provided a dose adjusted AUC of compound 1 of 11,800 ng/hr/ml, and a Cmax of 28,700 ng/ml. Compound 2 provided a dose adjusted AUC of compound 1 of 8,300 ng/hr/ml, and a Cmax of 19,200 ng/ml Compound 1 itself provided a dose adjusted AUC of compound 1 of 700 ng/hr/ml, and a Cmax of 1,900 ng/ml.

Results

It can be seen from the results shown above that compounds 2-6 have the ideal bioavailability profile of providing much higher plasma levels of the parent $A_{2B}$ adenosine receptor antagonist (compound 1) following oral dosing than is obtained by oral dosing of the parent compound (formula 1) itself. Additionally, no trace of the prodrug is seen in plasma. This is in marked contrast to compounds 6-11, which provide plasma levels of the parent $A_{2B}$ adenosine receptor antagonist following oral dosing that are lower than those obtained by oral dosing of the parent compound (formula 1) itself, and, in addition, compounds 6,8 and 10-11 are detected in the plasma unmetabolized. Compound 5 provided a bioavailability profile that is approximately the same as parent $A_{2B}$ adenosine receptor antagonist (compound 1).

What is claimed is:

1. A compound of the formula:

Formula I wherein:

$R^1$ and $R^2$ are independently lower alkyl;

$R^4$ is optionally substituted phenyl;

X is hydrogen or methyl; and

Y is —C(O)R, in which R is optionally substituted lower alkyl; or

Y is —P(O)(OR$^5$)$_2$, in which R$^5$ is hydrogen or lower alkyl; or a pharmaceutically acceptable salt thereof.

2. The compound of claim 1, wherein $R^1$ and $R^2$ are independently ethyl or n-propyl.

3. The compound of claim 1, wherein $R^4$ is 3-(trifluoromethyl)phenyl.

4. The compound of claim 3, wherein $R^1$ is n-propyl and $R^2$ is ethyl.

5. The compound of claim 4, wherein X is hydrogen.

6. The compound of claim 5, wherein Y is —C(O)R.

7. The compound of claim 6, wherein R is methyl, ethyl, n-propyl, isopropyl, n-butyl, isobutyl, t-butyl, or n-pentyl.

8. The compound of claim 7, wherein R is methyl, namely [3-ethyl-2,6-dioxo-1-propyl-8-(1-{[3-(trifluoromethyl)phenyl]methyl}pyrazol-4-yl)-1,3,7-trihydropurin-7-yl]methyl acetate.

9. The compound of claim 7, wherein R is n-propyl, namely [3-ethyl-2,6-dioxo-1-propyl-8-(1-{[3-(trifluoromethyl)phenyl]methyl}pyrazol-4-yl)-1,3,7-trihydropurin-7-yl]methyl butanoate.

10. The compound of claim 7, wherein R is t-butyl, namely [3-ethyl-2,6-dioxo-1-propyl-8-(1-{[3-(trifluoromethyl)phenyl]methyl}pyrazol-4-yl)-1,3,7-trihydropurin-7-yl]methyl 2,2-dimethylpropanoate.

11. The compound of claim 5, wherein Y is —P(O)(OR$^5$)$_2$.

12. The compound of claim 11, wherein R$^5$ is hydrogen, namely [3-ethyl-2,6-dioxo-1-propyl-8-(1-{[3-(trifluoromethyl)phenyl]methyl}-pyrazol-4-yl)(1,3,7-trihydropurin-7-yl)]methyl dihydrogen phosphate.

13. A method of treating a disease state chosen from diarrhea and asthma in a mammal, comprising administering to a mammal in need thereof a therapeutically effective dose of a compound of claim 1.

14. The method of claim 13, wherein the compound of claim 1 is chosen from the group consisting of
[3-ethyl-2,6-dioxo-1-propyl-8-(1-{[3-(trifluoromethyl)phenyl]methyl}pyrazol-4-yl)-1,3,7-trihydropurin-7-yl]methyl acetate,
[3-ethyl-2,6-dioxo-1-propyl-8-(1-{[3-(trifluoromethyl)phenyl]methyl}pyrazol-4-yl)-1,3,7-trihydropurin-7-yl]methyl butanoate,
[3-ethyl-2,6-dioxo-1-propyl-8-(1-{[3-(trifluoromethyl)phenyl]methyl}pyrazol-4-yl)-1,3,7-trihydropurin-7-yl]methyl 2,2-dimethylpropanoate, and
[3-ethyl-2,6-dioxo-1-propyl-8-(1-{[3-(trifluoromethyl)phenyl]methyl}-pyrazol-4-yl)(1,3,7-trihydropurin-7-yl)]methyl dihydrogen phosphate.

15. The method of claim 13, wherein the disease state is asthma.

16. The method of claim 13, wherein the disease state is diarrhea.

17. A pharmaceutical composition comprising at least one pharmaceutically acceptable excipient and a therapeutically effective amount of a compound of claim 1.

* * * * *